US008956653B2

(12) United States Patent
Bilgic

(10) Patent No.: US 8,956,653 B2
(45) Date of Patent: Feb. 17, 2015

(54) PREPARATIONS FOR EFFERVESCENT FORMULATIONS COMPRISING CEPHALOSPORIN AND USES THEREOF

(76) Inventor: Mahmut Bilgic, Istanbul (TR)

(\*) Notice: Subject to any disclaimer, the term of this patent is extended or adjusted under 35 U.S.C. 154(b) by 0 days.

(21) Appl. No.: 13/561,635

(22) Filed: Jul. 30, 2012

(65) Prior Publication Data

US 2013/0028844 A1 Jan. 31, 2013

Related U.S. Application Data

(63) Continuation-in-part of application No. PCT/TR2011/000029, filed on Jan. 28, 2011, and a continuation-in-part of application No. PCT/TR2011/000038, filed on Jan. 31, 2011.

(30) Foreign Application Priority Data

Jan. 29, 2010 (TR) .............................. a 2010 00688

(51) Int. Cl.
| | | |
|---|---|---|
| *A61K 9/46* | (2006.01) | |
| *A61K 31/545* | (2006.01) | |
| *A61K 31/424* | (2006.01) | |
| *A61K 31/43* | (2006.01) | |

(52) U.S. Cl.
CPC .............. *A61K 9/0007* (2013.01); *A61K 31/424* (2013.01); *A61K 31/43* (2013.01); *A61K 31/545* (2013.01)
USPC ......... 424/466; 424/44; 514/200; 514/210.04

(58) Field of Classification Search
None
See application file for complete search history.

(56) References Cited

U.S. PATENT DOCUMENTS

2003/0109503 A1   6/2003  Smith et al.
2007/0196477 A1\*  8/2007  Withiam et al. .............. 424/465

FOREIGN PATENT DOCUMENTS

| CN | 100417383 C | 9/2008 |
| EP | 0862915 A1 | 9/1998 |
| WO | WO 9116893 A1 \* | 11/1991 |
| WO | WO 9300898 A1 \* | 1/1993 |
| WO | WO-94/16696 A1 | 8/1994 |
| WO | WO-96/07408 A1 | 3/1996 |
| WO | WO 9607408 A1 \* | 3/1996 |
| WO | WO-98/34598 A2 | 8/1998 |
| WO | WO-99/49868 A1 | 10/1999 |
| WO | WO-2007/086012 A1 | 8/2007 |

OTHER PUBLICATIONS

International Search Report for PCT/TR2011/000029, mailed Nov. 4, 2011 (3 pages).
International Search Report for PCT/TR2011/000038, mailed Nov. 4, 2011 (3 pages).
Search Report of Turkish Patent Application TR 2010/00688, dated May 19, 2011 (9 pages).

\* cited by examiner

*Primary Examiner* — H. Sarah Park
(74) *Attorney, Agent, or Firm* — Clark & Elbing LLP

(57) ABSTRACT

The present invention relates to a process for preparing effervescent dosage forms comprising at least one antibiotic of cephalosporin group. The present invention also relates to effervescent formulations and preparations comprising antibiotics of second generation cephalosporin.

13 Claims, No Drawings

PREPARATIONS FOR EFFERVESCENT FORMULATIONS COMPRISING CEPHALOSPORIN AND USES THEREOF

CROSS-REFERENCE TO RELATED APPLICATIONS

This application is a continuation-in-part of PCT/TR2011/000029, filed Jan. 28, 2011, and PCT/TR2011/000038, filed Jan. 31, 2011, which are incorporated herein by reference in their entireties. This application is entitled to and claims priority benefits to application Serial Number TR2010/00688, filed Jan. 29, 2010.

BACKGROUND OF THE INVENTION

Cephalosporin and Formulations

Cephalosporins are beta lactam antibiotics that are commonly used in bacterial infections. Like other beta lactam antibiotics they show bactericid effect. The bacterial effect of cephalosporins is based on the inhibition of the synthesis of the bacteria cell wall. They inhibit cell wall synthesis by specifically binding to penicillin binding proteins (PBPs) which are present in the inner side of bacteria cell wall. As a result of inhibiting the cell wall synthesis related to PBPs, cephalosporins cause cell fractionation with the help of autolysins in the cell wall.

The formulations comprising cephalosporin group antibiotic can also be produced in the effervescent form, which is easy and safe to use for the patient and can provide the therapeutic activity and bio-availability that are provided by oral and suspension dosage forms.

For the preparation of the cephalosporin antibiotics in this dosage form, some methods are suggested in the prior art. These are dry granulation, wet granulation and dry blending methods. For instance, the patent numbered in WO2008057058 discloses the dry granulation method for the production of an antibiotic of cephalosporin group as active agent in solid dosage form. It is known that cephalosporins have a problem of wettability. Most of the medicaments included in this group are highly hydrophobic, thus they do not readily dissolve in water. Moreover, it is also known that cephalosporin antibiotics exhibit an unstable behavior upon contact with water. For these reasons, in the prior art dry granulation method is used in the preparation of the formulations comprising an antibiotic of cephalosporin group.

However, when dry granulation method is used for preparation of the formulation comprising a cephalosporin antibiotic in the form of a water dispersible dosage form, for example effervescent form, instead of solid oral dosage form, for example tablet; it is seen that harder and less porous granules are obtained. Having a harder and less porous structure of the granules can lead to obtaining dosage forms that do not homogeneously dissolve in water, for instance the agglomeration is observed in the obtained suspension or the granules forming the suspension precipitate in a short time. Therefore, these granules disperse in the water in such a way that the obtained suspension is agglomerated.

Wet granulation method that is suggested as an alternative is not preferred since effervescent acid and base give an effervescent reaction upon contact with water while they are wetted by aqueous granulation solutions and consequently carbon dioxide gas evolution is observed in the production process. Furthermore, carbon dioxide gas evolution resulting from the reaction of effervescent acid and base during the granulation prevents formation of that desirable effervescent reaction that should be obtained during the use of the final product. Therefore, this case causes a decrease in the absorption and bioavailability of cephalosporin antibiotic since the sufficient amount of carbon dioxide, which provides absorption of the active agent by increasing its permeability, is not given off.

As is seen, new approaches are needed for developing production methods of effervescent formulations comprising cephalosporin antibiotics.

As a result of the studies toward this requirement, the inventors have developed new formulations by using wet granulation method wherein formulations prepared according to the process of present invention are readily soluble and homogeneously dispersible in water; have high bioavailability and form a fluent and smooth suspension upon dispersion in water.

One aspect of said formulation is that the granulation solution that is used for preparation of formulations according to present invention comprises water in an amount in the range of 5-25%, preferably in the range of 8-20%, more preferably in the range of 10-18% and a pharmaceutically acceptable organic solvent.

In addition to water and organic solvent granulation solution may further comprise at least one pharmaceutical excipient, preferably a binder.

The inventors have surprisingly found that effervescent formulations, that are prepared by using the granulation solution comprising water in an amount in the range of 5-25%, preferably 8-20%, more preferably 10-18% by weight, have sufficiently hard and porous structure; are readily soluable; provide fluid and smooth suspension upon dispersion in water and have high bioavailability.

Second Generation Cephalosporins

Second generation cephalosporins indicate antibacterial effect on both gram positive and gram negative bacteria and have a wider gram negative spectrum compared to first generation cephalosporins. At the same time they are resistant to beta lactamase.

Antibiotics such as cefoxitin, cefamandol, cefotetan, cefuroxime, cefprozil and cefaclor are included in second generation cephalosporin group. These antibiotics of cephalosporin group are agents which are commonly used in the treatment of upper and lower respiratory diseases, sinusitis and otitis.

Formulations comprising antibiotic of second generation cephalosporin group are commonly present in form of oral tablet, oral suspension and capsule. However, solid dosage forms, wherein large amounts of antibiotic are formulated with the excipients, have a big size and this makes their use inconvenient for the patients. For that reason, as an alternative effervescent forms, which are reliable and easy to use for the patient, which are able to provide the therapeutic effect and bio-availability provided by oral suspension dosage form, are suggested.

In the prior art, it is known that at least one acid and one base are required for the preparation of effervescent formulations. Effervescent base reacts with effervescent acid in an aqueous medium and leads to evolution of carbon dioxide gas. The carbon dioxide gas evolution with bubbling provides rapid dispersion of the effervescent form in water and dissolution of the active agent easily. At the same time, carbon dioxide released as a result of effervescent reaction provides a higher absorption of the active agent by widening the intercellular space and thus increases bioavailability.

However, since the appropriate acidity is not maintained while using conventional effervescent formulations comprising an antibiotic of second generation cephalosporin group, effervescent base cannot react with acid efficiently and sufficient carbon dioxide gas evolution cannot be provided. This case makes the dissolution of antibiotic difficult and leads to decrease in the absorption and bioavailability.

As is seen, it is necessary to develop new formulations in order to provide that drugs in effervescent form comprising antibiotic of second generation cephalosporins easily dissolves upon contact with water, maintain acidity of the medium at optimum level and accordingly have a high absorption and bioavailability.

The inventors have surprisingly found that the problems in the prior art can be solved by the effervescent formulations developed in accordance with the present invention.

DETAILED DESCRIPTION OF THE INVENTION

Formulations Comprising at Least One Antibiotic of Cephalosporin

The present invention is related to a process for the preparation of the effervescent dosage forms comprising at least one antibiotic of cephalosporin group.

In accordance with the present invention, the process for preparation of effervescent formulations comprising at least one antibiotic of cephalosporin group comprises the following steps:
a. obtaining the granulation solution by adding 30-60%, preferably 40-55% of the total amount of binder into the granulation solvent;
b. sieving one effervescent acid and one effervescent base;
c. sieving a taste regulator;
d. adding sieved effervescent acid, effervescent base obtained from step b., the sieved taste regulator obtained from Step c. and 40-70%, preferably 45-60% of total amount of binder into the fluidized bed dryer and granulating them by the granulation solution prepared in step a;
e. drying and sieving the granules obtained in Step d;
f. mixing at least one cephalosporin antibiotic and one sweetener and adding the mixture into the granules obtained in Step d. after sieving;
g. adding flavoring agent and lubricant to the mixture obtained in Step f. and mixing;
h. optionally, compressing the final mixture into tablets in the tablet pressing machine.

In the process for the preparation of the formulations according to the present invention, lubricant can be added in step g. as it is described above and it can also be added into the granulation solution together with binder in Step a.

As a result of the preparation of effervescent formulations comprising at least one cephalosporin antibiotic in accordance with the present invention by using wet granulation method, the problems observed in dry granulation are not encountered. Moreover, it is seen that the obtained granules have sufficiently hard and porous structure for providing effective dispersion and absorption and the final product forms a suspension which is not agglomerated, by disintegrating homogeneously when it is released into water. Furthermore, when said amount of water is used in the granulation solution in the effervescent formulations prepared by wet granulation method, the problems described in the prior art, such as that carbon dioxide gas evolution and foaming resulting from the effervescent reaction between effervescent acid and base in aqueous media during the production have not been encountered. Accordingly, it is seen that desirable effervescent reaction occurs effectively during the use of final product and sufficient amount of carbon dioxide gas is emitted; the permeability of active agent increases and thus it is absorbed effectively.

In the first step of the process for preparation of the effervescent formulations in accordance with the present invention, it is aimed to prepare a granulation solution comprising water and an organic solvent as a first step of obtaining effervescent granules. In addition to this, by adding a pharmaceutically acceptable excipient, preferably a binder, into the granulation solution it was aimed to build bridges between the powder particles and hence an effective granulation was developed. A part of the used binder is added to the granulation solution in this step.

Optionally, lubricant can also be added into the granulation solution in this step.

In cases where a binder is used in the production of the effervescent formulation comprising at least one cephalosporin antibiotic, the inventors have seen that the use of binder leads to an increase in the dispersion time of the obtained effervescent medication; some problems are encountered during its handling or medication when in tablet form is not hard enough for a homogeneous dispersion. As a result of the studies conducted to solve these problems, when 30-60%, preferably 40-55% of the total amount of binder is added to granulation solution and the rest of the binder is added to dryer in the fourth step of the process, they have obtained effervescent formulations which are suitable for handling and carrying; which have suitable hardness and which disperse in water quickly.

In this aspect, the present invention is related to a process wherein 30-60%, preferably 40-55% of binder is added to the granulation solution and the rest of binder is added to the powder mixture that will be granulated with this granulation solution.

Organic solvent, which is used in the granulation solution in addition to water in the effervescent formulation in accordance with the present invention, can be selected from aliphatic and/or aromatic alcohols, glycols, ketones and esters.

In wet granulation method, since the granules obtained by the granulation of powder particles with granulation solution are not sufficiently dried during the drying process, agglomeration of these granules is observed and these agglomerations inhibit homogeneous dispersion of the final product. Moreover, when water is used as the only granulation solution in wet granulaiton method, it is possible that these added excipients absorb water and a swollen mass is formed instead of separate granules.

The inventors have not faced with the problems in the drying process that are present in the prior art, when they use volatile and non-toxic organic solvent in addition to water in the granulation solution in the process for preparation of said effervecent formulation. Said organic solvent can be selected from, but not limited with, a group comprising alcohols, preferably methanol, ethanol, prophanol, cethyl alcohol, ethylene glycol, glycerinor combinations thereof. More preferably ethanol is used.

In cases where ethanol is used as organic solvent in the granulation solution in the effervescent formulation in accordance with the present invention, the most suitable ratio of water to ethanol is found to be in the range of 1:1 to 1:15, preferably 1:2 to 1:10, more preferably 1:5 to 1:8 by weight in order to obtain stable granules in the most effective way.

In this aspect, the present invention is related to a process for the preparation of effervescent formulations wherein the ratio of water to ethanol that is used in the granulation solution is in the range of 1:1 and 1:15, preferably 1:2 and 1:10, more preferably 1:5 and 1:8 by weight.

In the second stage of the preparation of effervescent formulations in accordance with the present invention, an effervescent acid and base are added in order to obtain a formulation in effervescent form and they are sieved by using a sieve having sieve size under 3 mm, preferably in the range of 1-2 mm in order to get rid of possible agglomerated particles within these excipients.

For the purpose of preventing an unfavourable taste in the final product, in the third stage of the process for preparation of effervescent formulations in accordance with the present invention, a taste regulator is sieved and added to the effervescent couple.

In the fourth stage of the process for the preparation of effervescent formulations in accordance with the present invention, a powder mixture comprising effervescent couple, taste regulator and 40-70%, preferably 45-60% of total amount of binder is fed into the fluidized bed dryer. Said powder mixture is granulated with the granulation solution prepared in the first step. In this step, the low moisture ratio they limits the formation pre-effervescent reaction is kept constant by applying granulation and drying processes simultaneously.

In the fifth step, the obtained granules are dried at a temperature under 100° C., preferably at a temperature in the range of 45-80° C., more preferably at a temperature in the range of 55-75° C. until the moisture of the product is under 2%, preferably in the range of 0.1-1.5% in order to obtain harder and more stable granules. After that, the dried granules are sieved by using a sieve that has sieve size under 3 mm, preferably in the range of 1-2 mm in order to get rid of possible agglomerated particles within these excipients.

In the sixth step, at least one cephalosporin antibiotic and at least one pharmaceutically acceptable excipient, preferably sweetener, are mixed and the mixture is sieved by using a sieve that size sieve size under 3 mm, preferably in the range of 1-2 mm and added to the granules obtained in Step d.

In the final step, the final mixture is obtained by adding at least one pharmaceutically acceptable excipient, preferably at least one flavoring agent and/or lubricant and this mixture is optionally compressed into tablets in the tablet pressing machine. In this step, it is aimed to impart a pleasant taste to the final product by adding preferably flavoring agent.

The term "Effervescent formulations" comprises effervescent tablets, effervescent granules and effervescent powders.

The term "Effervescent couple" means the use of an acidic agent and a basic agent together.

The term "Granulation solvent" means a mixture of solvents comprising water and an organic solvent.

The term "Cephalosporin antibiotics" comprises first generation cephalosporins such as cephalexin, cephaloglycin, cephadroxyle, cephalothin, cefazoline, cephradine, cefroxadine and cefatrizine; the second generation cephalosporins such as cefoxitin, cefamandole, cefotetan, cefuroxime, cefprozil and cefaclor and third generation cephalosporins such as ceftriaxone, cefixime, cefoperazone, cefpodoxime, cefodizime, cefotaxime, ceftizoxime, cefdinir and cefsulodin. Preferably, cefaclor, cefuroxime, cefixime, cefprozil, cefdinir, cefpodoxime, more preferably cefprozil and/or cefaclor is used.

The term "Final product" means the final state of the effervescent tablet, effervescent granule or effervescent powder which is ready for use and which is obtained by producing effervescent formulations comprising at least one cephalosporin antibiotic in appropriate dosage forms.

Effevecent formulations in accordance with the present invention are in the form of effervescent granule, powder or tablet, preferably in tablet form.

Cephalosporin antibiotic that is used in the effervescent formulation in accordance with the present invention can be present in the form of its pharmaceutically acceptable hydrates, solvates, esters, enantiomers, polymorphs, crystal and/or amorphous forms, salts or in free form and/or as a combination thereof.

Cefaclor can be present in the form of its pharmaceutically acceptable esters, solvates, hydrates, enantiomers, racemates, organic salts, inorganic salts, polymorphs, crystal and/or amorphous forms or in free form and/or as a combination thereof.

Cefuroxime can be present in the form of its pharmaceutically acceptable esters, solvates, hydrates, enantiomers, racemates, organic salts, inorganic salts, polymorphs, crystal and/or amorphous forms or in free form and/or as a combination thereof. Preferably cefuroxime axetil is used.

Cefixime can be present in the form of its pharmaceutically acceptable esters, solvates, hydrates, enantiomers, racemates, organic salts, inorganic salts, polymorphs, crystal and amorphous forms or in free form and/or as a combination thereof. Before granulation, cefixime can be present in monohydrate, dihydrate or trihydrate form.

Cefdinir can be present in the form of its pharmaceutically acceptable esters, solvates, hydrates, enantiomers, racemates, organic salts, inorganic salts, polymorphs, crystal and/or amorphous forms or in free form and/or as a combination thereof.

Cefpodoxime can be present in the form of its pharmaceutically acceptable esters, solvates, hydrates, enantiomers, racemates, organic salts, inorganic salts, polymorphs, crystal and/or amorphous forms or in free form and/or as a combination thereof. Preferably cefpodoxime proxetil is used.

Cefprozil can be present in the form of its pharmaceutically acceptable esters, solvates, hydrates, enantiomers, racemates, organic salts, inorganic salts, polymorphs, crystal and/or amorphous forms or in free form and/or as a combination thereof.

Effervescent formulation in accordance with the present invention can optionally comprise one or more of excipients selected from a group comprising effervescent acid, effervescent base, binder, glidant, lubricant, diluents, disintegrant, flavoring agent, sweetener and/or taste regulator, coloring agent, surfactant, anti-foaming agent, humectants, acidic agent, basic agent and stabilizing agent.

Effervescent acid that is used in the effervescent formulation according to the present invention is selected from organic acids such as citric acid, tartaric acid, malic acid, fumaric acid, ascorbic acid, adipic acid, succinic acid and acetylsalicylic acid.

Effervescent base that is used in the effervescent formulation according to the present invention can be selected from sodium hydrogen carbonate, sodium carbonate, sodium bicarbonate, potassium carbonate, potassium bicarbonate, potassium hydrogen carbonate, sodium glycine carbonate, lysine carbonate, arginine carbonate and calcium carbonate.

Binder that is used in the effervescent formulation in accordance with the present invention can be selected from, but not limited with, a group comprising ethyl cellulose, gelatin, hydroxyethyl cellulose, hydroxymethyl cellulose, hydroxypropyl cellulose, hypromellose, magnesium aluminium silicate, methylcellulose, polyvinylpyrrolidone and povidone. Preferably polyvinylpyrrolidone is used.

Lubricant that is used in the effervescent formulation in accordance with the present invention can be selected from, but not limited with, a group comprising PEG 6000, polyvinyl alcohol, potassium benzoate, sodium benzoate.

Flavoring agent that can be used in effervescent formulations of the present invention can be selected from, but not limited with, natural aroma oils (peppermint oil, oil of wintergreen, oil of cloves, parsley oil, eucalyptus oil, lemon oil, orange oil), menthol, menthane, anethole, methyl salicylate, eucalyptole, cinnamon, 1-methyl acetate, sage, eugenol, oxanon, alpha-irison, marjoram, lemon, orange, blackberry, propenyl guaethol acethyl, cinnamon, vanilla, thymol, linalol, cinnamalaldehyde glycerol acethal, N-quadric p-menthan-3-carboxamide, 3,1-methoxy propane1,2-diol or a combination thereof.

Sweetener and/or taste regulator that can be used in effervescent formulations of the present invention can be selected from, but not limited with, a group of acesulfame, aspartame, dextrose, fructose, xylitol, saccharine, sucralose, sucrose, saccharin sodium, lactitol, maltitol, maltose, sorbitol, sodium cyclamate, sucrose and xylitol or a combination thereof.

In the effervescent formulation in accordance with the present invention, compared to the total weight of the unit dose, at least one cephalosporin antibiotic or its pharmaceutically acceptable solvates, hydrates, enantiomers, racemates, esters, organic salts, inorganic salts, polymorphs, crystal and/or amorphous forms and/or a combination thereof in an amount in the range of 5-75%, of effervescent acid in an amount in the range of 10-90%, effervescent base in an amount in the range of 5-80%, binder in an amount in the range of 0.5-30%, lubricant in an amount in the range of 0.1-6%, sweetener in an amount in the range of 0.1-6%, taste regulator in an amount in the range of 0.5-10%, and flavoring agent in an amount in the range of 0.2-7% can be present.

In another aspect, the present invention is related to the use of effervescent formulations comprising cephalosporin antibiotic for the upper respiratory tract infections such as pharangitis, tonsillitis, otitis media, sinusitis; lower respiratory tract infections such as secondary bacterial infections of acute bronchitis, acute bacterial inflammation of chronical bronchitis and pneumonia; skin and soft-tissue infections such as erysipelas, impetigo and apse, meningitis, septicaemia, endocarditis (endocardium infection) and urinary tract infections.

Effervescent formulations in accordance with the present invention can be prepared according to the following examples provided that they are not limited by these examples.

EXAMPLE 1

Formulation and Process for Preparation of Effervescent Tablets Comprising Cefprozil

| Component name | % amount in unit dose |
|---|---|
| Cefprozil | 30% |
| Effervescent acid | 35% |
| Effervescent base | 26% |
| Binder | 3.2% |
| Sweetener | 0.9% |
| Lubricant | 0.9% |
| Taste regulator | 2.8% |
| Flavoring Agent | 1.2% |

The process for preparation of pharmaceutical formulation comprising 30% of cefpozil in unit dose comprises the following steps:
1. The granulation solution is obtained by mixing deionized water and alcohol and adding 40% of the total amount of binder to the mixture
2. Effervescent acid and effervescent base is sieved.
3. Taste regulator is sieved 4. The effervescent acid, effervescent base obtained in step 2 and taste regulator in obtained in Step 3 and 60% of the total amount of binder are added into the fluidized bed dryer and granulating them by the granulation solution prepared in step 1;
5. The granules obtained in Step 4 are dried at 70° C. until the product moisture becomes 0.5% and then sieved.
6. Cefprozil and sweetener are blended and the obtained mixture is sieved and then mixed with the granules obtained in step 5.
7. Flavoring agent and lubricant are added to the mixture obtained in step 6 and mixed.
8. Optionally, the final mixture compressed into tablet in the tablet pressing machine.

Formulations Comprising Second Generation Cephalosporin

The present invention is related to effervescent formulations comprising a second generation cephalosporin antibiotic and process for the preparation of these formulations. Surprisingly, when a second acid is used in addition to organic acid which is used as effervescent acid in said effervescent formulation, effervescent forms that dissolve appropriately, that provide an efficient effervescent reaction and that have a high absorption and bioavailability are obtained.

Accordingly, the first aspect of the present invention is that effervescent formulations comprising a second generation cephalosporin antibiotic comprises a second effervescent acid in addition to organic acid used as effervescent acid.

Effervescent acid that is used in the effervescent formulation in accordance with the present invention is selected from, but not limited with, a group comprising citric acid, tartaric acid, malic acid, fumaric acid, ascorbic acid, acetic acid, adipic acid, succinic acid, acetylsalicylic acid and/or sodium citrate, sodium acetate, dibasic sodium phosphate, tribasic sodium phosphate, monobasic sodium phosphate, sodium acid pyrophosphate and sodium acid sulphite or a combination thereof.

Second generation cephalosporin antibiotics comprise cefoxitin, cefamandol, cefotetan, cefuroxime, cefprozil and cefaclor. In the effervescent formulations in accordance with the present invention, preferably cefaclor, cefprozil, cefuroxime, more preferably cefaclor is used as active agent.

Cefprozil can be present in the form of its pharmaceutically acceptable esters, solvates, hydrates, enantiomers, racemates, organic salts, inorganic salts, polymorphs, crystal and/or amorphous forms or in free form and/or as a combination thereof.

Cefuroxime can be present in the form of its pharmaceutically acceptable esters, solvates, hydrates, enantiomers, racemates, organic salts, inorganic salts, polymorphs, crystal and/or amorphous forms or in free form and/or as a combination thereof. Preferably cefuroxime axetil is used.

Cefaclor can be present in the form of its pharmaceutically acceptable esters, solvates, hydrates, enantiomers, racemates, organic salts, inorganic salts, polymorphs, crystal and/or amorphous forms or in free form and/or as a combination thereof.

Cefaclor that is used in the present invention can be present in one of the forms of monohydrate, dihydrate, trihydrate and/or anhydrous. Preferably, it is present in monohydrate form.

Another aspect of the present invention is the effervescent formulation comprising an antibiotic of second generation cephalosporin in an amount in the range of 1-60%, preferably 5-45% and more preferably 10-40% with respect to the total dosage weight.

Effervescent formulation in accordance with the present invention may comprise a second generation cephalosporin antibiotic and two different effervescent acids and in addition to these at least one of the excipients selected from a group comprising effervescent base, binder, glidant, lubricant, diluent, disintegrant, flavoring agent, sweetener and/or taste regulator.

Effervescent base that is used in the effervescent formulation in accordance with the present invention can be selected from, but not limited with, basic agents such as sodium hydrogen carbonate, sodium carbonate, sodium bicarbonate, potassium carbonate, potassium bicarbonate, potassium hydrogen carbonate, sodium glycine carbonate, lysine carbonate, arginine carbonate and calcium carbonate. Preferably, sodium hydrogen carbonate is used.

Binder that is used in the effervescent formulation in accordance with the present invention can be selected from, but not limited with, a group comprising; ethyl cellulose, gelatin, hydroxyethyl cellulose, hydroxymethyl cellulose, hydroxypropyl cellulose, hypromellose, magnesium aluminium silicate, methyl cellulose, polyvinylpyrrolidone and povidone. Preferably povidone is used.

Glidant that is used in the effervescent formulation in accordance with the present invention can be selected from, but not limited with, sodium lauryl sulfate, sodium benzoate, sodium chloride, sodium acetate, sodium fumarate, carbowax 4000, L-leucine(17), PEG or a combination thereof.

Lubricant used in the effervescent formulation in accordance with the present invention can be selected from, but not limited with, a group comprising PEG 6000, polyvinyl alcohol, potassium benzoate, sodium benzoate. Preferably, PEG 6000 is used.

Surfactant used in the effervescent formulation in accordance with the present invention can be selected from a group comprising sodium lauryl sulfate, sodium sulfate anhydrous and magnesium lauryl sulfate. Preferably, sodium sulfate anhydrous is used.

Diluent that can be used in effervescent formulations in accordance with the present invention can be selected from, but not limited with, a group comprising calcium carbonate, calcium sulfate, dibasic calcium phosphate, tribasic calcium phosphate, calcium sulfate, microcrystalline cellulose, lactose, magnesium carbonate, magnesium oxide, maltodextrin, maltose, mannitol, sodium chloride, sorbitol, starch and xylitol or combinations thereof.

Disintegrant that can be used in effervescent formulations in accordance with the present invention can be selected from, but not limited with, a group comprising carboxymethyl cellulose calcium, carboxymethyl cellulose sodium, microcrystalline cellulose, silicone dioxide, croscarmellose sodium, crospovidone, hydroxypropyl cellulose, methyl cellulose, povidone, magnesium aluminium silicate and starch or a combination thereof.

Flavoring agent that can be used in effervescent formulations of the present invention can be selected from, but not limited with, natural aroma oils (peppermint oil, oil of wintergreen, oil of cloves, parsley oil, eucalyptus oil, lemon oil, orange oil), menthol, menthane, anethole, methyl salicylate, eucalyptole, cinnamon, 1-methyl acetate, sage, eugenol, oxanon, alpha-irison, marjoram, lemon, orange, blackberry, propenyl guaethol acethyl, cinnamon, vanilla, thymol, linalol, cinnamalaldehyde glycerol acethal, N-quadric p-menthan-3-carboxamide, 3,1-methoxy propane1,2-diol or a combination thereof.

Sweetener and/or taste regulator that can be used in effervescent formulations of the present invention can be selected from, but not limited with, a group comprising acesulfame, aspartame, dextrose, fructose, glycose, lactitol, maltitol, maltose, sorbitol, saccharin, saccharin sodium, sodium cyclamate, sucralose, sodium chloride, potassium chloride, sucrose, xylitol or a combination thereof. Preferably, sodium cyclamate and/or saccharin sodium is used.

Generally, one of the most important matters for the patient is the compatibility of drug with stomach and not constituting a problem during the use of the drug. For that reason, the prepared formulations should have properties such that the formulations will not damage the natural pH equilibrium of stomachs. While using the drug, the inconsistancy in pH value of the solution that forms upon releasing effervescent formulations into water and the formation of a basic solution of formulation influence the natural pH equilibrium of stomach negatively and damage the stomach. Therefore, inventors have observed that the problems in the prior art can be solved by using effervescent acid mixture which has a buffering capability and which is obtained by using a mixture of an organic acid and additionally any of the salt forms of this organic acid as effervescent acid in said formulations.

Accordingly, in the formulation in accordance with the present invention acetic acid, citric acid, phosphoric acid are used. Preferably citric acid is used.

Second effervescent acid is in the form of alkali metal or alkaline-earth metal salt of the organic acid. Accordingly, second acid used in the formulation can be selected from a group comprising sodium citrate, sodium acetate, dibasic sodium phosphate, tribasic sodium phosphate, monobasic sodium phosphate, sodium acid pyrophosphate and sodium acid sulphite.

In this aspect, the present invention is related to effervescent formulations comprising a second generation cephalosporin antibiotic which are prepared by using a citric acid as effervescent acid and additionally sodium citrate, that is the salt form of citric acid, as the second effervescent acid.

Inventors have found that the ratio of acid and the salt of this acid composing effervescent acid mixture has an influence on keeping the pH of the solution formed by releasing the drug in effervescent form in accordance with the present invention into water, at a constant value and the complete neutralization of the effervescent base. Accordingly, it has been observed that effervescent base neutralizes completely by reacting with acid efficiently and an appropriate solution for the stomach is formed by maintaining the acidity in cases where the ratio of organic acid used as effervescent acid to any of the salts of this organic acid is in the range of 1:7 to 2:1, preferably 1:5 to 1:1, more preferably 1:4 to 1:2.

Another aspect of the present invention is that effervescent formulation comprises a mixture having the ratio of organic acid used as effervescent acid to any of its salts is in the range of 1:7 to 2:1, preferably 1:5 to 1:1, more preferably 1:4 to 1:2.

Effervescent formulations can be in the form of effervescent tablet, effervescent granules or effervescent powder, preferably they are in effervescent tablet form.

In the effervescent formulation in accordance with the present invention, with respect to the total weight of the unit dosage, second generation cephalosporin antibiotic in an amount in the range of 1-60%, effervescent acid in an amount in the range of 5-20%, second effervescent acid in an amount in the range of 5-30%, effervescent base in an amount in the range of 5-25%, surfactant in an amount in the range of 1-18%, binder in an amount in the range of 0.3-7%, lubricant in an amount in the range of 2-10%, sweetener and/or taste regulator in an amount in the range of 0.5-6% and flavoring agent in an amount in the range of 1-5% can be present.

In the effervescent formulation comprising second generation cephalosporin antibiotic in accordance with the present invention, optionally a second active agent can be used. The second active agent can be selected from beta lactamase and cephalasporins, preferably clavulanic acid or its pharmaceutically acceptable derivatives are used.

Clavulanic acid used in the effervescent formulation comprising second generation cephalosporin antibiotic in accordance with the present invention, can be present in the form of its solvates, hydrates, enantiomers, racemates, organic salts, inorganic salts, polymorphs, crystal or amorphous forms or in free form and/or as a combination thereof. Preferably, potassium clavulanate is used.

Clavulanic acid and derivatives thereof (for example potassium clavulanate) are very sensitive to moisture. Therefore, in the pharmaceutical composition according to the present invention, potassium clavulanate is preferably used together with a humidity absorbing agent in a ratio of 1:1.

One or more than one of the following substances can be used as a humidity absorbing agent; silica; colloid silica, for instance colloidal silica anhydrous, magnesium trisilicate, powder cellulose, magnesium oxide, calcium silicate, Syloid®, starch, microcrystalline cellulose and talc.

In the effervescent formulation comprising second generation cephalosporin antibiotic in accordance with the present invention, potasium clavulanate is preferably used with syloid or microcrystalline cellulose in a ratio of 1:1.

In the effervescent formulation comprising second generation cephalosporin antibiotic in accordance with the present invention, with respect to the total weight of the unit dose, 5-80%, preferably 10-70%, of clavulanic acid or pharmaceutically acceptable salts, hydrates, solvates or a combination thereof in an amount equivalent to that can be used.

Another aspect of the present invention is that the pharmaceutical composition prepared according to the invention is used for the treatment of the diseases relative to the upper respiratory tract infections such as pharangitis, tonsillitis, otitis media; lower respiratory tract infections such as acute pneumonia, acute and chronic broncihia and urinary tract infections such as acute cystitis and cystourethritis.

Another aspect of the present invention is the process for the preparation of the effervescent formulations comprising second generation cephalosporin antibiotic in accordance with the present invention, which comprises the steps of obtaining the granulation solution by mixing at least one binder, at least one lubricant and deionized water, sieving two different effervescent acids, effervescent base and surfactant and granulating them with the granulation solution, adding active agent, sweetener and flavoring agent after drying and sieving the granules obtained in the second step and preferably compressing the final mixture into tablets in the tablet pressing machine.

In cases where effervescent formulations comprising second generation cephalosporin antibiotic comprise a second active agent, for example potassium clavulanate, the process used for the preparation of said formulation comprises the steps of;
1. Blending effervescent acid, effervescent base, sweetener and binder and granulating the mixture with water and then drying and screening the obtained granules,
2. Adding lubricant, potassium clavulanate:humidity absorbing agent (1:1) mixture, cephalosporin antibiotic, coloring agent and flavoring agent into the obtained granules and blending them. The obtained effervescent formulation is optionally compressed into tablets in the tablet pressing machine.

Though not limited with these examples, effervescent formulations in accordance with the present invention can be prepared according to the examples given below.

EXAMPLE 2

Formulation and Process for Preparation of Effervescent Formulation

A granulation solution comprising binder, lubricant and deionized water is prepared. Two different effervescent acids, effervescent base and surfactant are granulated with the granulation solution by adding them into fluid bed dryer. Cefaclor, sweetener and flavoring agent are added into the obtained mixture and this mixture is dried. Finally, the dried mixture is compressed into tablets.

| Component name | % amount in unit dose |
|---|---|
| Cefaclor | 21% |
| Effervescent acid | 19% |
| Effervescent acid | 24.5% |
| Effervescent base | 15% |
| Surfactant | 13% |
| Binder | 1% |
| Sweetener | 2.5% |
| Lubricant | 1.5% |
| Flavoring Agent | 2.5% |

EXAMPLE 3

Formulation and Process for Preparation of Effervescent Formulation

The mixture comprising effervescent acid, effervescent base, sweetener and binder is granulated with water in the fluid bed dryer. The obtained granules are dried and sieved. Lubricant, potassium clavulanate: humidity absorbing agent (1:1) mixture, cefaclor, coloring agent and flavoring agent are added into the obtained granules and blended. The obtained final mixture is compressed into tablets.

| Component name | % amount in unit dose |
|---|---|
| Cefaclor | 11.5% |
| potassium clavulanate:Syloid | 17% |
| Effervescent acid | 16.5% |
| Effervescent acid | 21.5% |
| Effervescent base | 15% |
| Surfactant | 12.5% |
| Binder | 1% |
| Sweetener | 2% |
| Lubricant | 1.5% |
| Flavoring Agent | 1.5% |

What is claimed is:

1. An effervescent pharmaceutical composition comprising: a second generation cephalosporin antibiotic, a first effervescent organic acid, a second effervescent acid, an effervescent base, and one or more compounds selected from the group consisting of a surfactant, a binder, a lubricant, a sweetener, a taste regulator, and a flavoring agent, wherein said first effervescent acid is an organic acid and said second effervescent acid is an alkali metal or alkaline-earth metal salt of said first effervescent acid; and wherein said composition further comprises potassium clavulanate and the ratio of said antibiotic to potassium clavulanate is 1 to about 1.5.

2. A pharmaceutical composition according to claim 1, wherein said first effervescent acid is selected from the group consisting of citric acid, tartaric acid, malic acid, fumaric acid, ascorbic acid, acetic acid, adipic acid, succinic acid, and acetylsalicylic acid.

3. A pharmaceutical composition according to claim 2, wherein said first effervescent acid is citric acid.

4. A pharmaceutical composition according to claim 1, wherein said second effervescent acid is sodium citrate.

5. A pharmaceutical composition according to claim 1, wherein said second generation cephalosporin antibiotic is selected from the group consisting of: cefoxitin, cefamandole, cefotetan, cefuroxime, cefprozil, and cefaclor.

6. A pharmaceutical composition according to claim 1, wherein said composition comprises a second generation cephalosporin antibiotic in an amount in the range of 10-40% with respect to the total weight of the unit dosage.

7. A pharmaceutical composition according to claim 1, wherein the ratio of the first effervescent acid to the second effervescent acid is in the range of 1:7 to 2:1.

8. A pharmaceutical composition according to claim 1, wherein said second generation cephalosporin antibiotic is present in an amount of 1-60%, said first effervescent acid is present in an amount of 5-20%, said second effervescent acid is present in an amount of 5-30%, said effervescent base is present in an amount of 5-25%, said surfactant is present in an amount of 1-18%, said binder is present in an amount of 0.3-7%, said lubricant is present in an amount of 2-10%, said sweetener and/or taste regulator is present in an amount of 0.5-6%, and said flavoring agent is present in an amount of 1-5% by total weight of unit dosage.

9. The pharmaceutical composition according to claim 1, wherein said second generation cephalosporin antibiotic is cefuroxime.

10. The pharmaceutical composition according to claim 1, wherein said second generation cephalosporin antibiotic is cefprozil.

11. The pharmaceutical composition according to claim 1, wherein said second generation cephalosporin antibiotic is cefaclor.

12. A pharmaceutical composition according to claim 7, wherein the ratio of the first effervescent acid to the second effervescent acid is in the range of 1:4 to 1:2.

13. A pharmaceutical composition according to claim 7, wherein the ratio of the first effervescent acid to the second effervescent acid is in the range of 1:5 to 1:1.

* * * * *